United States Patent
Rinaldi et al.

(10) Patent No.: US 7,333,859 B2
(45) Date of Patent: Feb. 19, 2008

(54) RADIOELECTRIC ASYMMETRIC CONVEYER FOR THERAPEUTIC USE

(76) Inventors: Salvatore Rinaldi, Piazza G. Boccaccio 7, 50018 Scandicci (IT); Vania Fontani, Piazza G. Boccaccio 7, 50018 Scandicci (IT)

( * ) Notice: Subject to any disclaimer, the term of this patent is extended or adjusted under 35 U.S.C. 154(b) by 0 days.

(21) Appl. No.: 10/332,318

(22) PCT Filed: Jul. 6, 2001

(86) PCT No.: PCT/EP01/07800

§ 371 (c)(1),
(2), (4) Date: Jun. 3, 2003

(87) PCT Pub. No.: WO02/04069

PCT Pub. Date: Jan. 17, 2002

(65) Prior Publication Data

US 2004/0093048 A1     May 13, 2004

(30) Foreign Application Priority Data

Jul. 7, 2000     (IT) ............................. FI2000A0154

(51) Int. Cl.
*A61F 2/00*     (2006.01)

(52) U.S. Cl. ........................... 607/100; 607/96; 607/98; 607/99; 607/101; 606/32; 606/34

(58) Field of Classification Search ................ 607/100, 607/96, 98, 99
See application file for complete search history.

(56) References Cited

U.S. PATENT DOCUMENTS

| | | | |
|---|---|---|---|
| 4,121,592 A | * | 10/1978 | Whalley ...................... 607/98 |
| 4,197,851 A | * | 4/1980 | Fellus .......................... 607/71 |
| 5,507,743 A | | 4/1996 | Edwards et al. .............. 606/41 |

FOREIGN PATENT DOCUMENTS

CH           609866           3/1979

OTHER PUBLICATIONS

S. Rinaldi et al., "Neuro Psycho Physical Optimization with Conveyor of Modulating Radiance: New Strategy to Facilitate Rehabilitation", 1st International Congress of Neuroscience for Neruo Psycho Physical Optimization, Maison de l'U.N.E.S.C.O., Paris, Jul. 11-12, 2005, 9 pages.
S. Rinaldi et al., "A New Diagnostic and Therapeutic Approach to the General Adaptation Syndrome (G.A.S)", 11th World Congress of Psychophisiology, Montreal, Quebec, Canada, Jul. 29-Aug. 3, 2002, 1 page.

* cited by examiner

*Primary Examiner*—Linda C. M. Dvorak
*Assistant Examiner*—Matthew J. Kasztejna
(74) *Attorney, Agent, or Firm*—Abelman, Frayne & Schwab

(57) ABSTRACT

A radio-electric conveyer includes one or more radiofrequency generators supplied by a power group; one or more irradiating antennas coupled with the generator and which are able to create a radiofrequency field; a variable modulator; and one or more electrodes connected to generator and able to be applied to one or more predetermined parts of a body object of the therapy treatment, placed inside the field, in order to convey radiofrequency currents to the body.

21 Claims, 1 Drawing Sheet

RADIOELECTRIC ASYMMETRIC CONVEYER FOR THERAPEUTIC USE

FIELD OF THE INVENTION

The invention refers to the field of therapeutic Techniques and Physics Medicine and more particularly it refers to a device generating localised currents in the human body for therapeutic use.

STATE OF THE ART

As it is known the use of Electromagnetic field is a common practice in medical applications to both diagnostic and therapeutic aims.

In particular passive techniques are at the moment known which consist in the measuring of electric signals generated inside the human body (for example Electroencephalogram, Myography) and active techniques (for example microwave hyperthermia treatments, etc.).

On the other hand, the electromedical apparatus for electric stimulation are in general devices intended to induce currents circulating through the human body by the application of at least two electrodes which define the adduction points (Inlet/outlet) of the current flow to/from the body.

In the already known apparatus the electrodes are supplied by a current generator which can have a different nature depending on the specific application (for example perineal/muscular/antalgic Functional Electrostimulation etc.) and can be defined "symmetric" in respect to the electrodes position.

AIM OF THE INVENTION

A first aim is to obtain current distributions different from those which can be obtained using the traditional symmetric schemes.

SUMMARY OF THE INVENTION

This aim has been reached according to the invention by a radioelectric conveyer which is substantially constituted by a radiofrequency generator, a system of irradiating antennas (typically a single antenna) and by a group of electrodes to be placed on contact with any part, internal or external, of the body.

The conveyer makes use of a original connection in which the body of a patient is no more placed as a subject irradiated by the EM radiation but it is a part of the system of transmitting antennas where it is connected to the ground base antenna instead of to the emitting side of the system.

The system EM generator/Patient-living tissue is intended to be made in such a way that it is completely insulated from ground and from any conducting body or mass, in particular from metal mass.

The device of the invention has the function of generating weak radiofrequency currents which are conveyed and collect at the application points of the electrodes.

The electrodes can be applied to any point, group of points, zone or organic tissue of the body either externally or inside the same body, where the currents have to be conveyed.

The antennas are placed at a certain distance form the patient body, so that the same body is diffusely exposed to the Electromagnetic fields irradiated by the antennas.

Therefore, by the described device it is carried out an electrostimulation obtained by electrodes and antennas which form radiofrequency circuits determining the passage of weak currents towards the application points of the electrodes, at which points the same currents are collecting.

Substantially the currents are generated by the combined use of galvanic contact electrodes (as it happens in the traditional electrostimulation treatments) or capacitive contact electrodes and of antennas irradiating electromagnetic fields, according to a scheme which can be for that reason called "asymmetric".

In fact, unlike the traditional electrostimulation systems which are based uniquely on electrodes (symmetric scheme), the present device makes possible to generate currents which are concentrated at the application points of the electrodes but they flow being extremely diffused through the whole body subject to the electromagnetic radiation.

A first advantage is that by the device of the invention it is possible to convey weak currents to well localised points of a human or animal body by the simultaneous and combined use of electrodes and irradiating antennas.

A second advantage is that the radiation emitted by the antennas determines an extremely diffused exposition through the body, so that it is caused a circulation of currents conveyed and concentrated by the electrodes applied to the body.

A further advantage in respect to the prior art systems is the higher flexibility of the present apparatus which by changing the application points, the shape, and the number of the electrodes, makes it possible to have substantially any distribution of the current circulation.

DESCRIPTION OF THE DRAWINGS

These and still further advantages will be better understood by a man skilled in the art from the following description and the annexed drawings, given as a non limiting example, in which.

DETAILED DESCRIPTION

Figure 1:
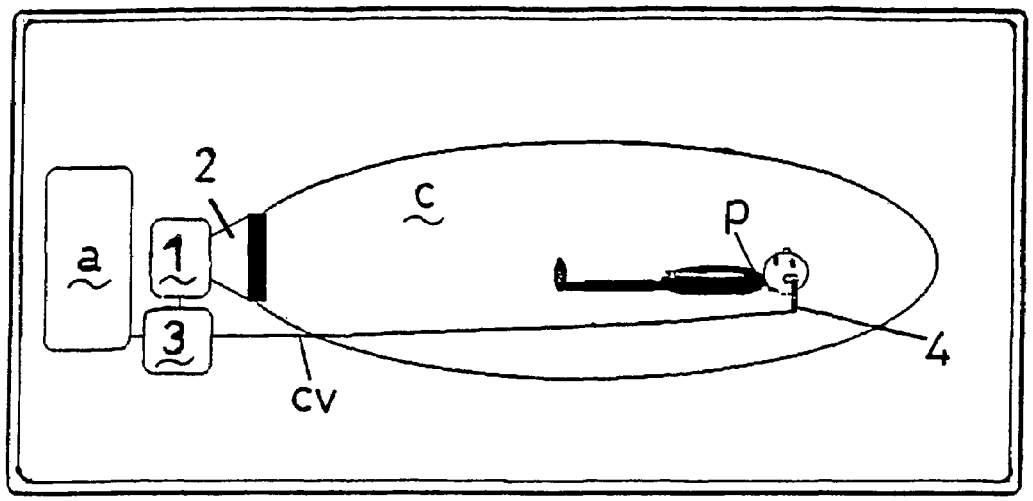
FIGS. 1, 2 respectively show the scheme of two possible embodiments of a radiofrequency conveyer according to the invention.

The conveyer substantially comprises:
a power assembly (a);
one or more radiofrequency generator 1;
one or more irradiating antennas 2;
a variable modulator 3;
one or more electrodes 4 to be applied or associated to selected parts of the body (p) subject to the therapy. The electrodes are connected through cables (cv) to the generator 1.

A substantial feature is that the system (s) as a whole, constituted by: supply assembly (a)/generator 1/coupler/modulator 3/antennas 2/electrodes 4/body (p) and operator, is constantly kept insulated from the ground and from any other connection to earth.

The generator is coupled to the electrostimulation circuit constituted by the antennas and by the electrodes; an end of the coupler is connected to antenna 2, the other one is connected to the electrodes 4. A modulation system permit the operator to suitably modulate by command the generator and the probe coupling. In the functioning, the radiofrequency field (c) generated by the generator 1 and irradiated by the system of antennas 2 pervades the environment obtaining a very diffused irradiation on and inside the body (p) (e.g the patient).

The electrodes 4 applied to the body determine a conveyed circulation of radiofrequency microcurrents concentrated in the application regions.

Patient (p) will be therefore subject to a flow of radiofrequency currents having frequency, time, modulation, and circulation as decided by the operator according to the specific medical protocol defined by the therapy.

Figure 2:
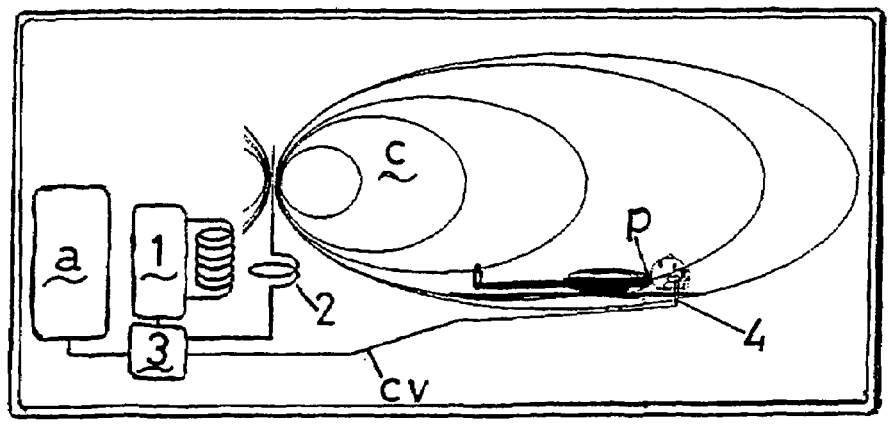

With reference to FIGS. 1 and 2, two possible schemes of the apparatus according to the invention are illustrated. The embodiments are made different by the type of radiofrequency generator and they comprise the radiofrequency generator apparatus with the coupling to the emitting circuit and to the electrodes system to conveying the radiofrequency currents in the body subject to the therapy.

The radiofrequency circuit comprises the system of antennas, the body placed inside the radiofrequency field generated by the generator and emitted by the same antennas, and the focusing of radiofrequency currents at the contact point of the electrodes with the body to delimit and to convey the dispersion of the radiofrequency currents.

It is evident that the above are principle schemes and that they refer to specific radiofrequency circuits, while they do not limit the technologic embodiments which can be possible for each the components (generator/s, couplers, antenna circuits, conductive elements, etc.).

It is also evident that the radioelectric several generators can be provided and operating at different frequencies, like the antennas or the low frequencies irradiating panels, electrostatic system comprised.

Preferably, modulators and flow switches can be provided on both the generator and the antenna circuit.

Several electrodes can be provided, of different shapes and size and made of different conductive, semi-conductive, insulating or mixed materials. The electrodes can be applied on single or multiple points or they can be applied for capacitive effect, being not placed to direct contact with the body of the patient.

In particular, according to the invention the electrodes 4 can have the shape of metal sheets preferably aluminium, which can be applied to wide regions of the patient's body.

In a preferred embodiment, given as a non limiting example, a conveyer according to the invention present the following characteristics:

Emitting Group of Irradiating Energy
Buncher resonator: GUNN effect diode Resonator
Angles of the emitting lobe: Horizontal 85°-Vertical 50°
Frequency band X—resonance frequency 10,525 GHz-Maximum emission power <10 mW
Components on printed circuits—SMT technology
Work voltage 5 Vcc.

Receiving/Detector Group
Receiving circuit—planar type
Detector: SCKOTTY Diode
Detector circuit: Mixer circuit
Value of the signal level to/from the detector: 40 mV min thermal working range +5° to +40°
Dimensions of the Receiving/Transmitting Group 48 L×40h×12W mm.

Irradiating Energy—Emission Lobe
The electromagnetic low power energy in band X is irradiated in a ellipsoidal lobe having angles of: 50° Vertical, 85° Horizontal.

In respect to noise, back echo caused by objects having a typical absorption, reflection frequency in the X band of the human tissues and a surface of approximately 0.5 m$^2$, effects can be appreciated by the detector thanks to the Doppler effect/Mixer circuit in the receiving system at the distance of 12 meters. Without considering the average typical reflection coefficients, the absorption of the constituting materials and taking not into account specific particulars possibly presents and which could make the filed less uniform, the average radiating electromagnetic energy produced by the Gunn cavity oscillator and distributed in the closed space of a 4 m×4 m×3 m room, typically a masonry room, can be valued in approximately $20 \times 10^{-11}$ W/cm$^3$.

In the use, a suitably programmed processing unit provides to determine the emitting steps of the electromagnetic energy in the room, according to the settings previously chosen by the operator.

For Example:

Manual Control by Probe:
Minimum emitting time: 10 ms
Maximum emitting time: 10 sec
Possible cyclic emission (discharge) by continuous command of the steps: predetermined time—pre-emission interval—predetermined time Keyboard Settings
Minimum emitting time: 10 ms
Maximum emitting time: 10 sec
Minimum time interval: 10 ms
Maximum time interval: 10 sec
Maximum number of intervals: 99
Sequence possibly interrupted by keyboard.

The present invention has been described with reference to a preferred embodiment but it is obvious that equivalent modifications can be made by a man skilled in the art without outgoing from the scope of the present invention.

The invention claimed is:

1. A radio-electric conveyer for the radio-electric electro-stimulation of a body (p) of a patient, the radio-electric conveyer comprising:
   at least one radiofrequency generator (1) powered by a power system (a), said radio frequency generator (1) having an emission power lower than 10 mW;
   at least one irradiating antenna (2) coupled to the at least one radiofrequency generator (1) and which is able to create a radiofrequency field (c), thereby generating a diffused irradiation towards the body (p) of the patient to be treated by therapy and placed inside the radiofrequency field (c), with the at least one irradiating antenna (2) being remotely located with respect to the body (p) and transmitting the diffused irradiation intended to radiate the whole of the body (p) of the patient;
   a variable modulator (3); and
   at least one electrode (4) connected to the at least one generator (1) and which is applied to at least one predetermined part of the body (p) of the patient to be treated by therapy and placed inside the radiofrequency field (c), in order to convey radiofrequency currents generated by the radiofrequency field (c) in the body (p), the radiofrequency field (c) conveying significantly highly diffused radiofrequency currents in the body (p);
   wherein each of the at least one electrode (4) are connected to said generator (1) which are applied to one or more predetermined parts of said body (p), whereby each of the at least one electrode (4) conveys radiofrequency currents generated by said radiofrequency field (c) in the body (p) with the radiofrequency currents being returned by the at least one electrode (4) to the at least one radiofrequency generator.

2. The conveyer according to claim 1, wherein said radiofrequency generator (1) emitted volume power density around said body (p) is approximately $20 \times 10^{-11}$ W/cm$^3$.

3. The conveyer according to claim 1, wherein the at least one electrode (4) is in the shape of a sheet.

4. The conveyer according to claim 3, wherein the at least one electrode (4) is made of a conductive material.

5. The conveyer according to claim 4, wherein the at least one electrode (4) is made of aluminum.

6. The conveyer according to claim 3, wherein the at least one electrode (4) is made of a non-conductive material.

7. The conveyer according to claim 1, wherein the at least one electrode (4) is applied for galvanic contact to the body (p).

8. The conveyer according to claim 1, wherein the at least one electrode (4) is applied for capacitive contact to the body (p).

9. The at least one electrode (4) for a conveyer according to claim 1, wherein the at least one electrode (4) has the shape of a sheet.

10. The at least one electrode (4) according to claim 9, wherein the at least one electrode (4) is made of a conductive material.

11. The at least one electrode (4) according to claim 10, wherein the at least one electrode (4) is made of aluminum.

12. The at least one electrode (4) according to claim 8, wherein the at least one electrode (4) is made of a non-conductive material.

13. The at least one electrode (4) according to claim 9, wherein the at least one electrode (4) is applied for galvanic contact to the body (p).

14. The at least one electrode (4) according to claim 9, wherein the at least one electrode (4) is applied for capacitive contact to the body (p).

15. A method for the radio-electric electrostimulation of a body (p) of a patient, the method comprising the following steps:
  generating a radiofrequency field (c) diffused through the body (p) of the patient to be treated by therapy and placed inside the radiofrequency field (c) using a radiofrequency generator (1) having an emission power lower than 10 mW, thereby generating a diffused irradiation toward the body (p) of the patient;
  positioning at least one irradiating antenna (2) remotely located with respect to the body (p);
  arranging the body (p) inside the radiofrequency field (c) to generate radiofrequency currents therein;
  transmitting the diffused irradiation from the remotely located at least one irradiating antenna (2) with the intention to radiate the whole of the body (p) of the patient; and
  applying to at least one predetermined part of the body (p) at least one electrode (4) connected to the radiofrequency generator (1), in order to convey the generated radiofrequency currents to the at least one predetermined part of the body (p), the radiofrequency field (c) conveying significantly highly diffused radiofrequency currents in the body (p); and
  returning, using the at least one electrode (4), the radiofrequency currents from the body (p) to the radiofrequency generator (1).

16. The method according to claim 15, wherein the at least one electrode (4) is applied for galvanic contact to the body (p).

17. The method according to claim 15, wherein the at least one electrode (4) is applied for capacitive contact to the body (p).

18. The radio-electric conveyer according to claim 1, wherein an emission power of the radiofrequency generator (1) is less than about 10 mW.

19. The method according to claim 15, wherein an emission power of the radiofrequency generator (1) is less than about 10 mW.

20. Radio-electric conveyer for the radio-electric electrostimulation of a body (p) of a patient, the radio-electric conveyer comprising:
  one or more radiofrequency generators (1) powered by a power system (a), wherein each respective emission power of the one or more radiofrequency generators (1) is lower than 10 mW;
  one or more irradiating antennas (2) coupled to the one or more radiofrequency generators (1) and which are able to create a radiofrequency field (c), thereby generating a diffused irradiation towards the body (p) of the patient to be treated by therapy and placed inside the radiofrequency field (c) with the at least one irradiating antenna (2) being remotely located with respect to the body (p) and transmitting the diffused irradiation intended to radiate the whole of the body (p) of the patient;
  a variable modulator (3); and
  one or more electrodes (4) connected to the one or more radiofrequency generators (1) and which are applied to or associated with one or more predetermined parts of the body (p) to be treated by therapy and placed inside the radiofrequency field (c), the radiofrequency field (c) conveying extremely diffused radiofrequency currents in the body (p) and whereby said one or more electrodes conveys said radiofrequency currents to be returned to said one or more radiofrequency generators.

21. The conveyer according to claim 1, wherein said radio-electric conveyor is insulated from the earth.

* * * * *